(12) United States Patent
Axelrod et al.

(10) Patent No.: US 12,029,650 B2
(45) Date of Patent: Jul. 9, 2024

(54) SYSTEM FOR TREATING HYPERTROPHIC CARDIOMYOPATHY AND LEFT VENTRICULAR OUTFLOW TRACT OBSTRUCTION

(71) Applicant: Edwards Lifesciences Corporation, Irvine, CA (US)

(72) Inventors: Noa Axelrod, Netanya (IL); Boaz Manash, Givat Ada (IL); David Maimon, Atlit (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 704 days.

(21) Appl. No.: 16/534,534

(22) Filed: Aug. 7, 2019

(65) Prior Publication Data

US 2020/0078175 A1    Mar. 12, 2020

Related U.S. Application Data

(60) Provisional application No. 62/727,655, filed on Sep. 6, 2018.

(51) Int. Cl.
*A61F 2/00*    (2006.01)
*A61F 2/24*    (2006.01)

(52) U.S. Cl.
CPC .... *A61F 2/2487* (2013.01); *A61F 2220/0008* (2013.01); *A61F 2220/0075* (2013.01); *A61F 2230/0006* (2013.01); *A61F 2230/0039* (2013.01); *A61F 2230/0091* (2013.01); *A61F 2250/0065* (2013.01)

(58) Field of Classification Search
None
See application file for complete search history.

(56) References Cited

U.S. PATENT DOCUMENTS

| | | | |
|---|---|---|---|
| 7,316,706 B2 | 1/2008 | Bloom et al. | |
| 7,695,493 B2* | 4/2010 | Saadat ............... | A61B 17/0644 606/198 |
| 7,766,816 B2 | 8/2010 | Chin et al. | |
| 7,798,953 B1 | 9/2010 | Wilk | |
| 8,491,455 B2 | 7/2013 | Annest et al. | |
| 8,870,916 B2 | 10/2014 | Ewers et al. | |
| 8,945,211 B2* | 2/2015 | Sugimoto ......... | A61B 17/00234 623/2.37 |
| 9,211,115 B2 | 12/2015 | Annest et al. | |
| 10,463,492 B2* | 11/2019 | Tylis .................... | A61B 8/0883 |
| 2003/0233022 A1 | 12/2003 | Vidlund et al. | |

(Continued)

FOREIGN PATENT DOCUMENTS

| | | | | |
|---|---|---|---|---|
| WO | WO-2009051682 A1 * | 4/2009 | ......... | A61B 17/0401 |
| WO | WO-2017106713 A1 * | 6/2017 | ......... | A61B 17/0401 |

*Primary Examiner* — John R Downey
*Assistant Examiner* — Anant A Gupta
(74) *Attorney, Agent, or Firm* — Chang & Hale LLP

(57) ABSTRACT

A cardiac device comprises a first anchoring element configured to be attached to a first side of a tissue wall, a second anchoring element configured to be attached to a second side of the tissue wall, and a cinching device. The cinching device is configured to attach to the first anchoring element and the second anchoring element and apply force to the first anchoring element to move the first anchoring element towards the second anchoring element and at least partially compress the tissue wall.

20 Claims, 13 Drawing Sheets

(56) References Cited

U.S. PATENT DOCUMENTS

| | | | |
|---|---|---|---|
| 2004/0148020 A1* | 7/2004 | Vidlund | A61F 2/2481 |
| | | | 623/2.11 |
| 2006/0052821 A1 | 3/2006 | Abbott et al. | |
| 2007/0066863 A1 | 3/2007 | Rafiee et al. | |
| 2007/0179527 A1* | 8/2007 | Eskuri | A61B 17/0057 |
| | | | 606/213 |
| 2013/0204175 A1* | 8/2013 | Sugimoto | A61M 27/002 |
| | | | 604/8 |
| 2015/0025553 A1 | 1/2015 | Del Nido et al. | |
| 2017/0135817 A1* | 5/2017 | Tylis | A61B 8/12 |
| 2017/0156864 A1 | 6/2017 | Chang et al. | |
| 2017/0340329 A1* | 11/2017 | Groothuis | A61B 17/0401 |

* cited by examiner

SYSTEM FOR TREATING HYPERTROPHIC CARDIOMYOPATHY AND LEFT VENTRICULAR OUTFLOW TRACT OBSTRUCTION

CROSS REFERENCE TO RELATED APPLICATION

This application claims priority to U.S. Provisional Application No. 62/727,655, filed on Sep. 6, 2018, entitled SYSTEM FOR TREATING HYPERTROPHIC CARDIOMYOPATHY AND LEFT VENTRICULAR OUTFLOW TRACT OBSTRUCTION, the disclosure of which is hereby incorporated by reference in its entirety.

BACKGROUND

Field

The present disclosure generally relates to the field of improving heart performance.

Description of Related Art

Hypertrophic Cardiomyopathy (HCM) is a disease in which a portion of the myocardium is hypertrophic, creating functional impairment of the heart. The occurrence of HCM is a significant cause of sudden cardiac death and a cause of disabling cardiac symptoms.

SUMMARY

In some implementations, the present disclosure relates to a cardiac device comprising a first anchoring element configured to be attached to a first side of a tissue wall, a second anchoring element configured to be attached to a second side of the tissue wall and a cinching device configured to attach to the first anchoring element and the second anchoring element and apply force to the first anchoring element to move the first anchoring element towards the second anchoring element and at least partially compress the tissue wall.

In certain embodiments, the first anchoring element has a cylindrical shape and a diameter of the first anchoring element is less than a height of the first anchoring element. The second anchoring element may have a disc shape, comprise two or more cylindrical rods, and/or comprise a coiled wire.

In some embodiments, the cinching device comprises a first telescoping element having a hollow structure and comprising a locking mechanism and a second telescoping element configured to fit into the first telescoping element and comprising a helical groove. The locking mechanism may be configured to fit into the helical groove to lock the cinching device in place. In some embodiments, each of the first telescoping element and the second telescoping element is configured to be at least partially embedded in the tissue wall. The first telescoping element may be configured to be situated outside of the tissue wall and the second telescoping element is configured to be at least partially embedded in the tissue wall.

The cinching device may comprise a threaded element configured to pass through the first anchoring element and the second anchoring element and a locking element configured to fit over the threaded element and move along the threaded element by twisting. In some embodiments, the locking element comprises a notch configured to receive a twisting tool.

In some embodiments, the cinching device comprises a first telescoping element having a hollow structure and comprising a helical groove and a second telescoping element configured to fit into the first telescoping element and comprising a locking mechanism, wherein the locking mechanism is configured to fit into the helical groove to lock the cinching device in place. Each of the first telescoping element and the second telescoping element may be configured to be at least partially embedded in the tissue wall.

The cinching device may comprise a threaded element and the first anchoring element may be configured to move along the threaded element by rotating around the threaded element. In some embodiments, the cinching device comprises two or more twisted sutures and a locking element at an end of the cinching device.

In some embodiments, the first anchoring element comprises one or more mini anchors configured to engage the tissue wall to prevent rotation of the first anchoring element. The tissue wall may be a septum.

In certain implementations, the present disclosure relates to a method comprising inserting a catheter into a ventricle of a heart and passing a cardiac device through the catheter. The cardiac device comprises a first anchoring element, a second anchoring element, and a cinching device attached to the first anchoring element and the second anchoring element. The method further comprises piercing a proximal side of a tissue wall, attaching the second anchoring element to a distal side of the tissue wall, attaching the first anchoring element to the proximal side of the tissue wall, tightening the cardiac device to at least partially compress the tissue wall, and locking the cardiac device in place. The cinching device may be at least partially embedded in the tissue wall. In some embodiments, the tissue wall may be a septum.

In some implementations, the present disclosure relates to a cardiac device comprising a first means for anchoring to a first side of a tissue wall, a second means for anchoring to a second side of the tissue wall, and a means for applying force to the first means for anchoring to move the first means for anchoring towards the second means for anchoring and at least partially compress the tissue wall, wherein the means for applying force is attached to the first means for anchoring and the second means for anchoring. In some embodiments, the tissue wall is a septum.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

DETAILED DESCRIPTION

The headings provided herein are for convenience only and do not necessarily affect the scope or meaning of the claimed invention.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Overview

In humans and other vertebrate animals, the heart generally comprises a muscular organ having four pumping chambers, wherein the flow thereof is at least partially controlled by various heart valves, namely, the aortic, mitral (or bicuspid), tricuspid, and pulmonary valves. The valves may be configured to open and close in response to a pressure gradient present during various stages of the cardiac cycle (e.g., relaxation and contraction) to at least partially control the flow of blood to a respective region of the heart and/or to blood vessels (e.g., pulmonary, aorta, etc.).

Figure 1:
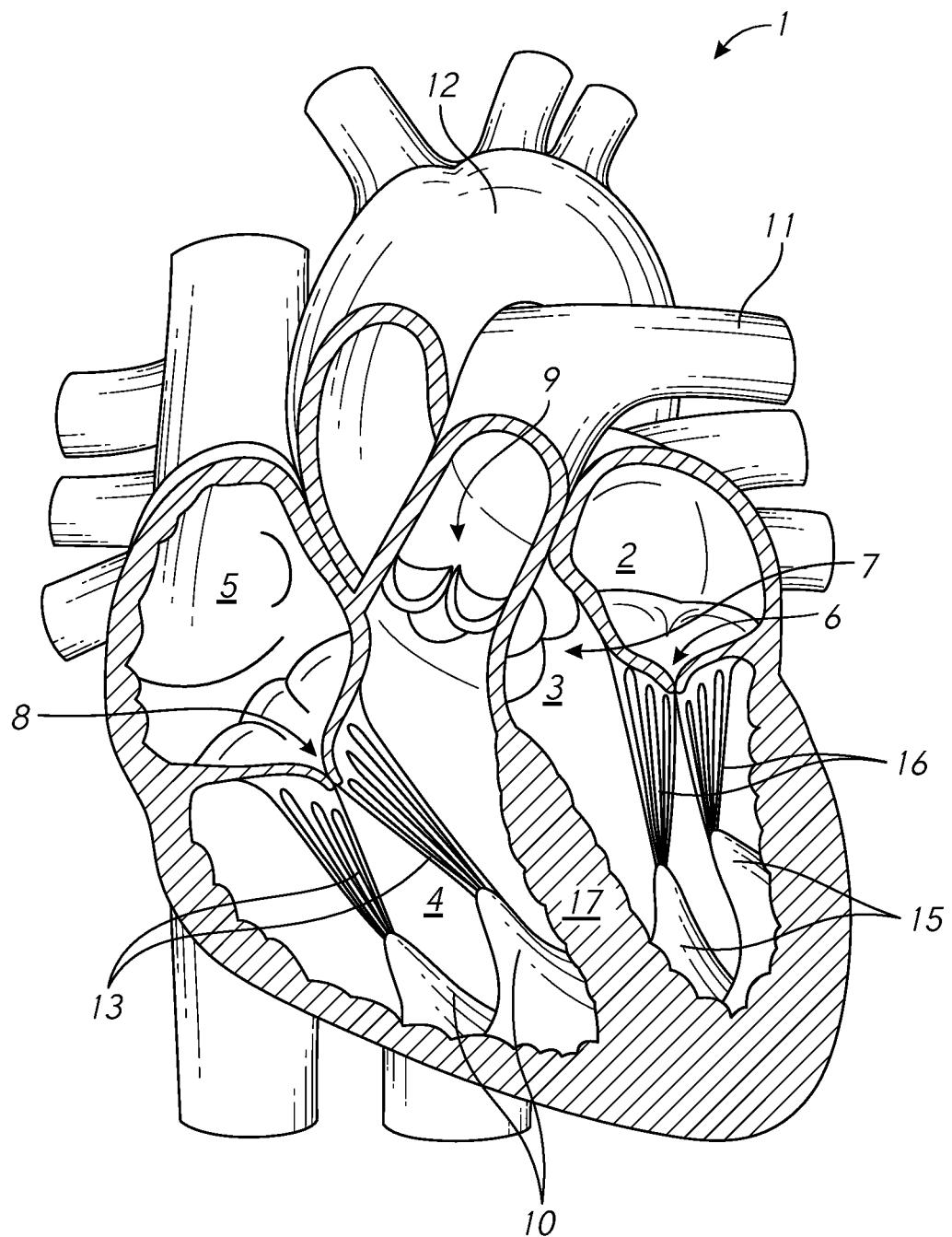
FIG. 1 provides a cross-sectional view of a human heart.

FIG. 1 illustrates an example representation of a heart 1 having various features relevant to certain embodiments of the present inventive disclosure. The heart 1 includes four chambers, namely the left atrium 2, the left ventricle 3, the right ventricle 4, and the right atrium 5. A wall of muscle 17, referred to as the septum, separates the left 2 and right 5 atria and the left 3 and right 4 ventricles. The heart 1 further includes four valves for aiding the circulation of blood therein, including the tricuspid valve 8, which separates the right atrium 5 from the right ventricle 4. The tricuspid valve 8 may generally have three cusps or leaflets and may generally close during ventricular contraction (i.e., systole) and open during ventricular expansion (i.e., diastole). The valves of the heart 1 further include the pulmonary valve 9, which separates the right ventricle 4 from the pulmonary artery 11, and may be configured to open during systole so that blood may be pumped toward the lungs, and close during diastole to prevent blood from leaking back into the heart from the pulmonary artery. The pulmonary valve 9 generally has three cusps/leaflets, wherein each one may have a crescent-type shape. The heart 1 further includes the mitral valve 6, which generally has two cusps/leaflets and separates the left atrium 2 from the left ventricle 3. The mitral valve 6 may generally be configured to open during diastole so that blood in the left atrium 2 can flow into the left ventricle 3, and advantageously close during diastole to prevent blood from leaking back into the left atrium 2. The aortic valve 7 separates the left ventricle 3 from the aorta 12. The aortic valve 7 is configured to open during systole to allow blood leaving the left ventricle 3 to enter the aorta 12, and close during diastole to prevent blood from leaking back into the left ventricle 3.

Heart valves may generally comprise a relatively dense fibrous ring, referred to herein as the annulus, as well as a plurality of leaflets or cusps attached to the annulus. Generally, the size of the leaflets or cusps may be such that when the heart contracts the resulting increased blood pressure produced within the corresponding heart chamber forces the leaflets at least partially open to allow flow from the heart chamber. As the pressure in the heart chamber subsides, the pressure in the subsequent chamber or blood vessel may become dominant, and press back against the leaflets. As a result, the leaflets/cusps come in apposition to each other, thereby closing the flow passage.

The atrioventricular (i.e., mitral and tricuspid) heart valves may further comprise a collection of chordae tendineae and papillary muscles for securing the leaflets of the respective valves to promote and/or facilitate proper coaptation of the valve leaflets and prevent prolapse thereof. The papillary muscles, for example, may generally comprise finger-like projections from the ventricle wall. With respect to the tricuspid valve 8, the normal tricuspid valve may comprise three leaflets (two shown in FIG. 1) and three corresponding papillary muscles 10 (two shown in FIG. 1). The leaflets of the tricuspid valve may be referred to as the anterior, posterior and septal leaflets, respectively. The valve leaflets are connected to the papillary muscles 10 by the chordae tendineae 13, which are disposed in the right ventricle 4 along with the papillary muscles 10. Although tricuspid valves are described herein as comprising three leaflets, it should be understood that tricuspid valves may occur with two or four leaflets in certain patients and/or conditions; the principles relating to papillary muscle repositioning disclosed herein are applicable to atrioventricular valves having any number of leaflets and/or papillary muscles associated therewith.

The right ventricular papillary muscles 10 originate in the right ventricle wall, and attach to the anterior, posterior and septal leaflets of the tricuspid valve, respectively, via the chordae tendineae 13. The papillary muscles 10 of the right ventricle 4 may have variable anatomy; the anterior papillary may generally be the most prominent of the papillary muscles. The papillary muscles 10 may serve to secure the leaflets of the tricuspid valve 8 to prevent prolapsing of the leaflets into the right atrium 5 during ventricular systole. Tricuspid regurgitation can be the result of papillary dysfunction or chordae rupture.

With respect to the mitral valve 6, a normal mitral valve may comprise two leaflets (anterior and posterior) and two corresponding papillary muscles 15. The papillary muscles 15 originate in the left ventricle wall and project into the left ventricle 3. Generally, the anterior leaflet may cover approximately two-thirds of the valve annulus. Although the anterior leaflet covers a greater portion of the annulus, the posterior leaflet may comprise a larger surface area in certain anatomies.

The valve leaflets of the mitral valve 6 may be prevented from prolapsing into the left atrium 2 by the action of the chordae tendineae 16 tendons connecting the valve leaflets to the papillary muscles 15. The relatively inelastic chordae tendineae 16 are attached at one end to the papillary muscles 15 and at the other to the valve leaflets; chordae tendineae from each of the papillary muscles 15 are attached to a respective leaflet of the mitral valve 6. Thus, when the left ventricle 3 contracts, the intraventricular pressure forces the valve to close, while the chordae tendineae 16 keep the leaflets coapting together and prevent the valve from opening in the wrong direction, thereby preventing blood to flow back to the left atrium 2. The various chords of the chordae tendineae may have different thicknesses, wherein relatively thinner chords are attached to the free leaflet margin, while relatively thicker chords (e.g., strut chords) are attached farther away from the free margin.

The ventricles of the heart 1 further include trabeculae carneae ("trabeculae" herein) associated with the inner ventricle walls. The trabeculae can comprise irregular bands and bundles of muscle associated with and/or projecting from the inner surfaces of the ventricles. The trabeculae may be concentrated at or near the apex of the ventricles, but may also span all or part of the inner walls (i.e., sidewalls) of the ventricles. The trabeculae may form prominent ridges, or gaps, which may be leveraged for inserting or weaving anchoring element features therein or therethrough, as described in detail below in connection with one or more embodiments of the present disclosure.

As mentioned above, the septum 17 is a wall of muscle that separates the left 2 and right 5 atria and the left 3 and right 4 ventricles. The septum 17 constitutes a major part of the heart and contributes to both left and right ventricular function. It is directly affected in certain disease states. Hypertrophic Cardiomyopathy (HCM) is a disease in which a portion of the myocardium (e.g., the septum 17) is hypertrophic (i.e., enlarged/thickened), creating functional impairment of the heart. The occurrence of HCM is a significant cause of sudden cardiac death in any age group and a cause of disabling cardiac symptoms. HCM can be treated by medication or, in severe cases, by myectomy or by alcohol septal ablation.

Figure 2A:
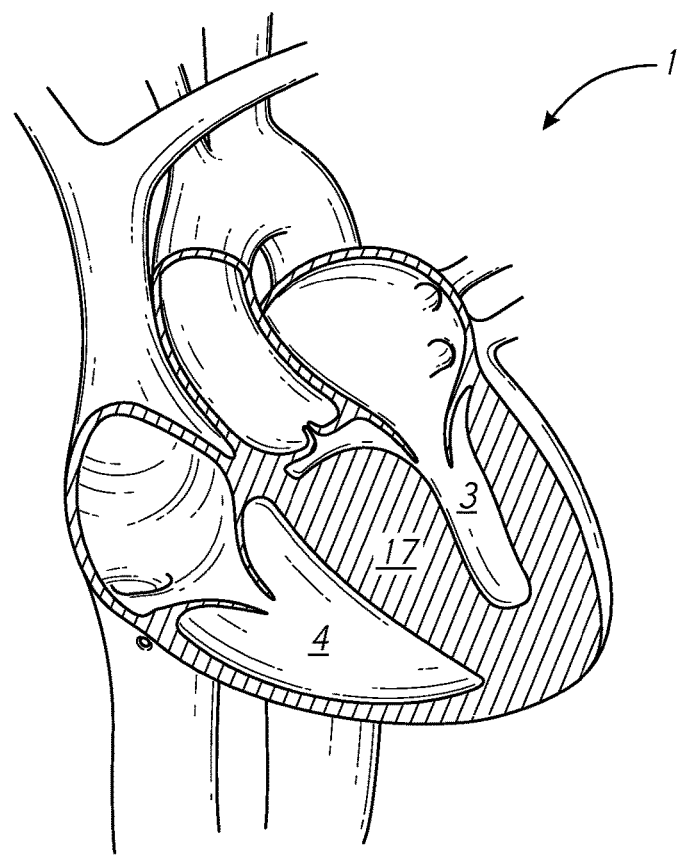
FIG. 2A provides a cross-sectional view of a heart experiencing Hypertrophic Cardiomyopathy (HCM).

FIG. 2A provides a cross-sectional view of a heart 1 experiencing HCM and/or similar conditions. As in the example shown in FIG. 2A, HCM may involve a thickened septum 17 (i.e., septal bulge) which may cause left ventricular outflow tract (LVOT) obstruction and/or other issues. LVOT obstruction may result in impeded blood flow. For example, an LVOT obstruction may obstruct blood flow through the aortic and/or mitral valves. Moreover, in some cases, a portion of the mitral valve may attach to and/or contact a thickened septum 17, further blocking blood flow.

Figure 2B:
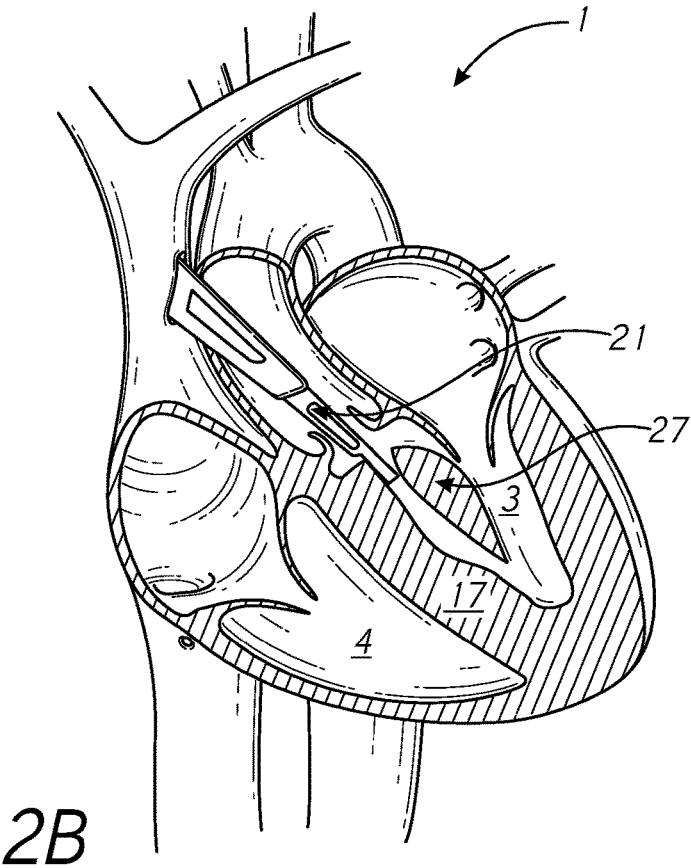
FIG. 2B provides a method of treating HCM.

Various techniques for treating HCM and/or related conditions including LVOT obstruction may suffer from certain drawbacks. For example, FIG. 2B provides a method of treating HCM in which a portion 27 of tissue is surgically removed from a thickened area (e.g., an LVOT obstruction at the septum 17) through use of a surgical tool 21. By removing the portion 27 of tissue, the LVOT to the aorta may be widened. Another method of treating HCM involves injecting alcohol through a catheter in an artery supplying blood to an affected area of heart muscle to destroy some of the thickened tissue. However, each of these techniques can be unpredictable and can cause various adverse effects. Additionally, for surgical procedures, it can be difficult or impossible to evaluate the efficacy of the repair prior to the conclusion of the operation.

Certain embodiments disclosed herein provide solutions for treating thickened portions of myocardium without the need for surgical procedures and/or without destroying cardiac tissue. In particular, passive techniques to improve blood flow are disclosed for improving cardiac function. Further, various embodiments disclosed herein provide for the treatment of HCM that can be executed on a beating heart, thereby allowing for the ability to assess the efficacy of the treatment and potentially implement various modifications thereto without the need for bypass support. In some cases (e.g., in which a portion of the mitral valve is attached to a thickened septum 17), the solutions described herein may be applied in connection with transcatheter mitral valve repair (TMVR) procedures.

In some embodiments, a mechanical device for treating HCM and/or other diseases may be delivered to an affected area of tissue via a transcatheter procedure. The device may comprise one or more anchors. For example, a device may include multiple anchors and each may be delivered to a side of a thickened tissue wall (e.g., one anchor positioned in the right ventricle and one anchor positioned in the left ventricle) and a cinching element connecting the anchors. The cinching element may be tightened to press the anchors together, thereby reducing a thickness of at least a portion of the tissue wall to create a channel through which blood may flow. For example, due at least in part to pressure applied by the cinching element and/or anchors at the tissue wall, the tissue may compress to some degree at least around the cinching element and/or anchors. The device may be delivered and adjusted using a transfemoral (artery), transapical, or transseptal procedure. Once in place, the device may be detached from the delivery system and left in the heart an implant.

In some embodiments, a portion of a thickened area of tissue, rather than the entire thickened area of tissue, may be compressed such that a thickness of the portion is reduced. For example, one or more anchors may be pressed into the tissue through use of a cinching element. In some cases, at least one of the anchors may have a smaller profile than the thickened area of tissue. Accordingly, the thickened area of tissue may experience a greatest amount of compression at the portions covered and/or in contact with an anchor, while portions of tissue around an anchor and/or not in contact with an anchor may experience a lesser amount of compression. In this way, a channel may be created around and/or through the portion to allow greater blood flow. By compressing only a portion of a thickened area of tissue, the thickness of the portion may be reduced to a greater extent than if the entire thickened area were compressed. For example, when a first portion of thickened area of a tissue wall is pressed, myocardium within the tissue wall at the first portion may be displaced to other portions of the tissue wall and the first portion may be compressed. When an entire thickened area of a tissue wall is pressed, there is less area for the myocardium to be displaced to and therefore very little compression may be created at the thickened area. In contrast, when only a portion of a thickened area of tissue is pressed (e.g., using anchors having a smaller profile than the thickened area of tissue), the myocardium in the portion can be displaced to other portions of the thickened area. Moreover, creation of a channel through a thickened area of tissue may be sufficient to create a substantial improvement in blood flow around and/or through the thickened area.

Compression Methods and Systems

Figure 3A:
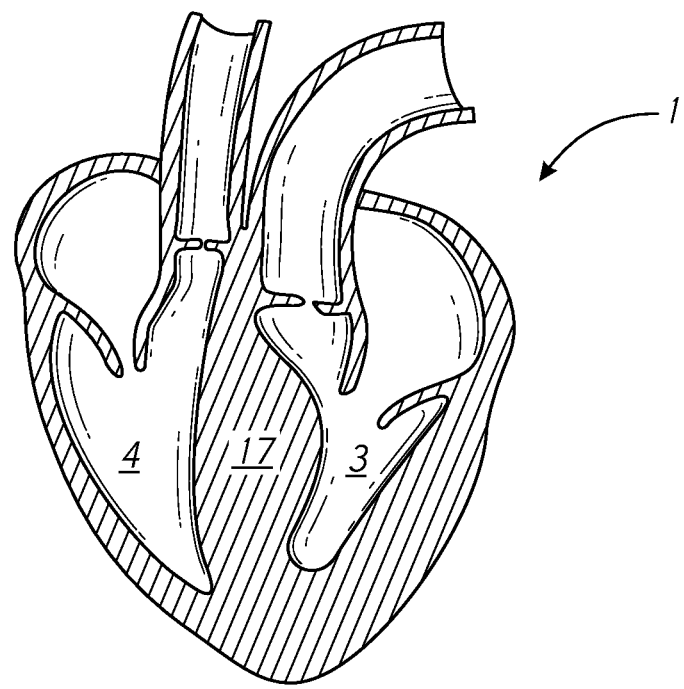
FIG. 3A provides a cross-sectional view of the heart having a thickened septum.
Figure 3B:
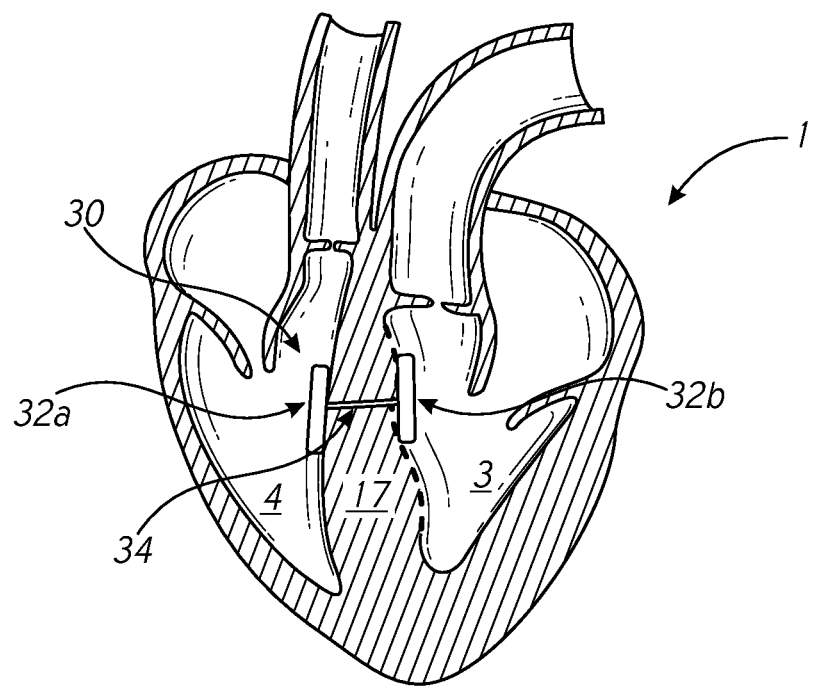
FIG. 3B provides a cross-sectional view of the heart with a device which may be used to compress at least a portion of the thickened septum in accordance with some embodiments.

FIG. 3A provides a cross-sectional view of the heart 1 having a thickened septum 17. FIG. 3B provides a cross-sectional view of the heart 1 with a device 30 which may be used to compress at least a portion of the thickened septum 17. The device 30 comprises a first anchoring element 32A and a second anchoring element 32b. While the device 30 is shown in certain figures as having two anchoring elements, embodiment devices may have a single anchoring element or more than two anchoring elements. The first anchoring element 32a may be anchored to the right ventricle 4 side of the septum 17 and the second anchoring element 32b may be anchored to the left ventricle 3 side of the septum 17. The anchoring elements may be situated in a ventricle and/or may be at least partially embedded in the septum 17. In certain embodiments, the device 30 may be anchored to areas of tissue other than the septum 17.

The anchoring elements 32a, 32b may be composed of metal, plastic, polymer, Teflon, Nitinol, felt, or other material. In some embodiments, the anchoring elements 32a, 32b may be composed of an at least partially rigid material in order to maintain a desired level of pressure at the septum 17 or other tissue area.

In some embodiments, the first anchoring element 32a and second anchoring element 32b may be connected by a cinching device 34. Example embodiments of the cinching device 34 are described herein in further detail with respect to FIGS. 7A-7F. In some embodiments, the cinching device 34 may comprise one or more lengths of material attached to one or more of the first anchoring element 32a and second anchoring element 32b. Each of the one or more lengths of material may be a suture, string, cord, wire, band, tube, or other similar device. In some embodiments, the cinching device 34 may comprise one or more flexible or rigid mechanisms and/or may be capable of tightening (e.g., cinching) to decrease a distance between the first anchoring element 32a and second anchoring element 32b. The cinching device 34 may be connected to one or both anchoring elements and/or may pass through cavities in one or both anchoring elements. In some embodiments, the cinching device 34 may be configured to be tightened and locked into place through use of a locking element or otherwise.

In some embodiments, the device 30 may be configured to create a channel and/or indentation through the thickened area of tissue. The channel and/or indentation may have any shape and/or may be oriented in any direction. For example, a channel may have an elongate linear form in which a length of the channel is greater than a width of the channel. The channel may be oriented such that as blood flows downward (i.e., from the top of the page to the bottom of the page of the heart 1 shown in FIG. 3B) from the aortic valve and/or upward into the aortic valve, the blood may be configured to pass through the length of the channel.

Figure 4A:
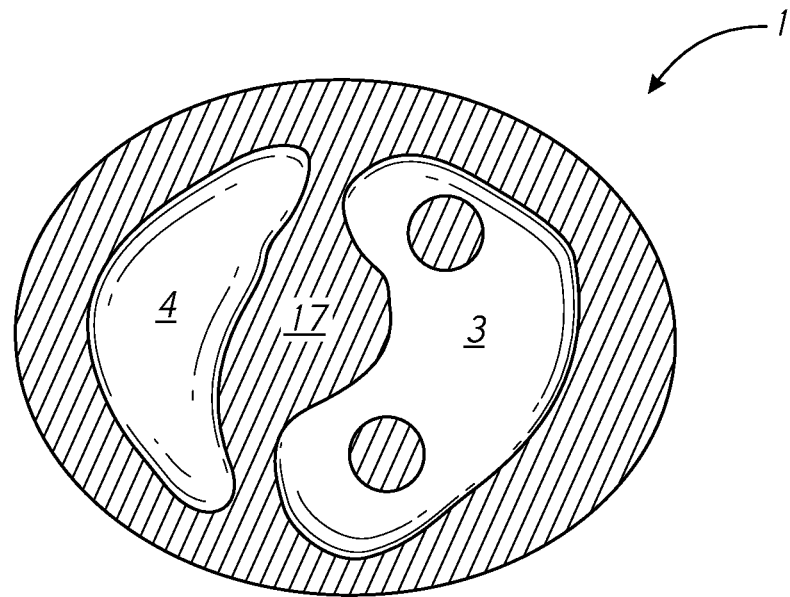
FIG. 4A provides another cross-sectional view of the heart having a thickened septum.
Figure 4B:
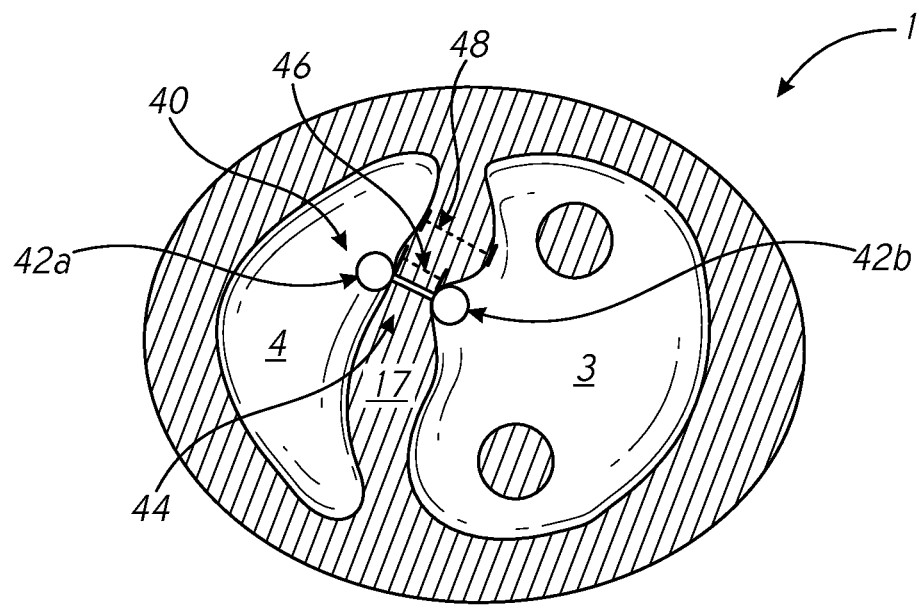
FIG. 4B illustrates a device which may be used to compress at least a portion of the thickened septum in accordance with some embodiments.

FIG. 4A provides another cross-sectional view of the heart 1 having a thickened septum 17. FIG. 4B illustrates a device 40 which may be used to compress at least a portion of the thickened septum 17. The device 40 comprises a first anchoring element 42a and a second anchoring element 42b. The first anchoring element 42a may be anchored to the right ventricle 4 side of the septum 17 and the second anchoring element 42b may be anchored to the left ventricle 3 side of the septum 17. The anchoring elements may be situated in a ventricle or may be embedded in the septum 17.

The first anchoring element 42a and second anchoring element 42b may be connected by a cinching device 44. The cinching device 44 may be connected to one or both anchoring elements and/or may pass through cavities in one or both anchoring elements. In some embodiments, the cinching device 44 may be configured to be tightened and locked into place through use of a locking element or otherwise.

The device 40 may be configured to compress a portion of the septum 17 such that a first thickness 46 of the septum 17 at or near the device 40 is less than a second thickness 48 (e.g., a maximum thickness) of the septum 17. In this way, the device 40 creates a flow channel at or around the device 40 to improve blood flow in the left ventricle 3 and/or right ventricle 4.

In some embodiments, the first anchoring element 42a and/or second anchoring element 42b may be sized and/or shaped to not cover an entire thickened portion of tissue. For example, the second anchoring element 42b (on the left ventricle 3 side) may have a shape of a cylindrical rod (e.g., in which the diameter of the rod is less than the height of the rod) to create a thin channel in the thickened portion of tissue. In some embodiments, the first anchoring element 42a and/or second anchoring element 42b may be sized and/or shaped to distribute pressure across a greater area of tissue. For example, the first anchoring element 42a (on the right ventricle 4 side) may have a disc-shape to more effectively distribute pressure with minimal imprint to the tissue. Non-limiting examples of suitable anchoring elements are illustrated in FIGS. 6A-6D and 7A-7F. In some embodiments, suitable anchor types may include balloon anchors (e.g., filled with polymer) and Amplatzer-like meshes and may have any suitable shape (e.g., an umbrella shape).

In some embodiments, the device may be configured to create a channel and/or indentation through the thickened area of tissue. The channel and/or indentation may have any shape and/or may be oriented in any direction. For example, a channel may have an elongate linear form in which a length of the channel (e.g., into the page of FIG. 4B) is greater than a width of the channel. The channel may be oriented such that as blood flows downward (i.e., into the page of the heart 1 shown in FIG. 3B) from the aortic valve and/or upward into the aortic valve, the blood may be configured to pass through the length of the channel.

Compression Device Delivery Processes

FIGS. 5A-5F illustrate steps of a process for delivering compression devices to a heart 1 according to one or more embodiments disclosed herein. While some steps illustrated in FIGS. 5A-5F may be directed to delivery through the aortic valve 7 into the left ventricle 3, such steps may also be applied to delivery into the left ventricle 3 through the mitral valve and/or into the right ventricle 4 through the pulmonary valve 9 or the tricuspid valve 8.

Figure 5A:
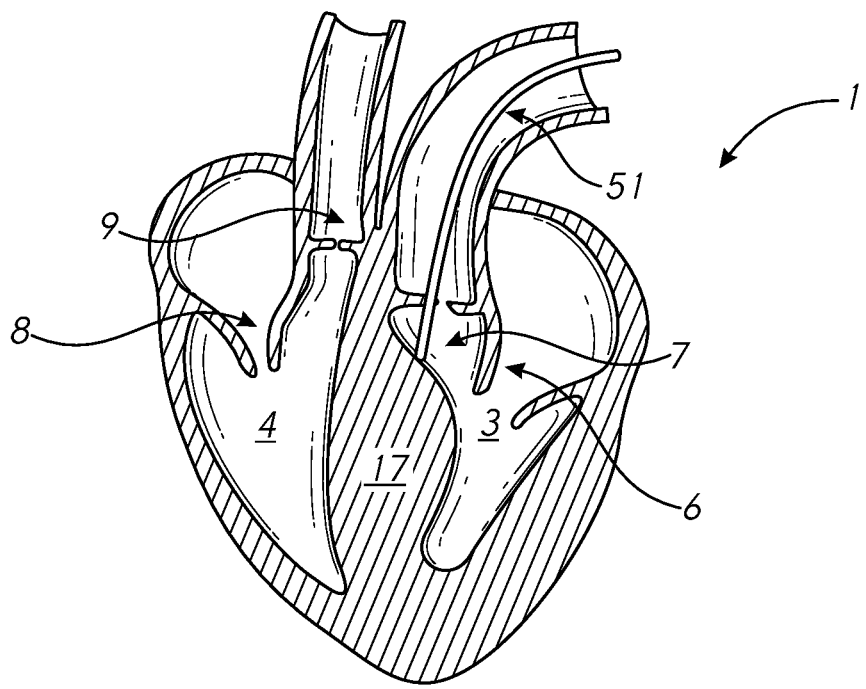
FIGS. 5A-5F illustrate steps of a process for delivering compression devices to a heart according to one or more embodiments disclosed herein.

As shown in FIG. 5A, a catheter 51 (e.g., a transfemoral catheter) may be fed through the aortic valve 7 into the left ventricle 3 near a thickened area of the septum 17. By delivering the catheter 51 into the left ventricle 3, needles and/or other devices may be passed through the catheter 51 to penetrate the septum 17 from the left ventricle 3 side and may protrude from the septum 17 on the right ventricle 4 side. In this way, potential damage caused by protruding devices may be reduced. For example, when a device penetrates the septum 17 and/or other tissue wall, it can be difficult to predict where the device will exit the tissue wall. Due to the proximity of the mitral valve 6 to a thickened septum 17 in some cases, a device entering the septum 17 from the right ventricle 4 side and exiting the septum 17 from the left ventricle 3 side may create a risk of damaging mitral valve 6 leaflets and/or other tissue. This risk may be reduced by entering the septum 17 from the left ventricle side 3 in some cases.

Figure 5B:
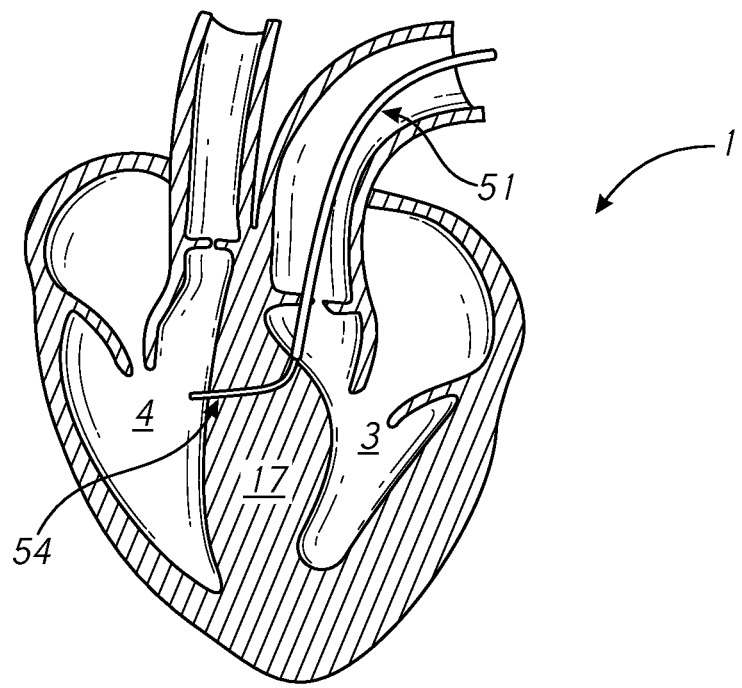

In FIG. 5B, a device (e.g., a transseptal needle) is introduced to pass through the septum 17 from the left ventricle 3 to the right ventricle 4. The device may have a curved form and/or may be composed of a flexible material. In some embodiments, the device may be used in connection with a dilator and/or sheath (e.g., a tube) to deliver the device and/or penetrate the septum 17. After the device punctures the septum 17, at least a portion of the dilator and/or sheath may penetrate the septum 17. The sheath may be left at least partially in the left ventricle 3. In some embodiments, a guidewire may be passed through the septum 17 (e.g., through the sheath) to guide one or more anchoring elements and/or lines. The catheter 51 may be sized to accommodate the various devices. For example, the catheter 51 may have a diameter of at least 12 French to fit an anchoring element having a diameter equal to or less than 12 French.

Figure 5C:
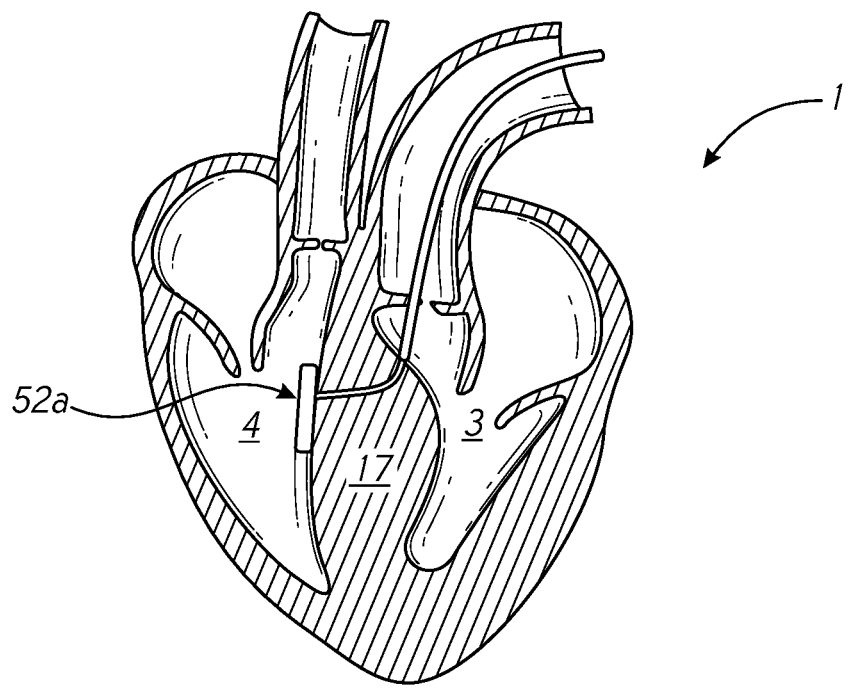

As shown in FIG. 5C, a first anchoring element 52a may be passed through the septum 17 (e.g., through a sheath) and anchored to the septum 17 wall on the right ventricle side 4. In some embodiments, the first anchoring element 52a and/or second anchoring element 52b may have a compressed (e.g., lower profile) form during delivery in order to fit through a catheter or similar device and may expand after delivery. For example, the first anchoring element 52a may be composed of Nitinol or another material with shape-memory characteristics. In some embodiments, the first anchoring element 52a may be pre-attached to a cinching device 54, guidewire, or other device.

Figure 5D:
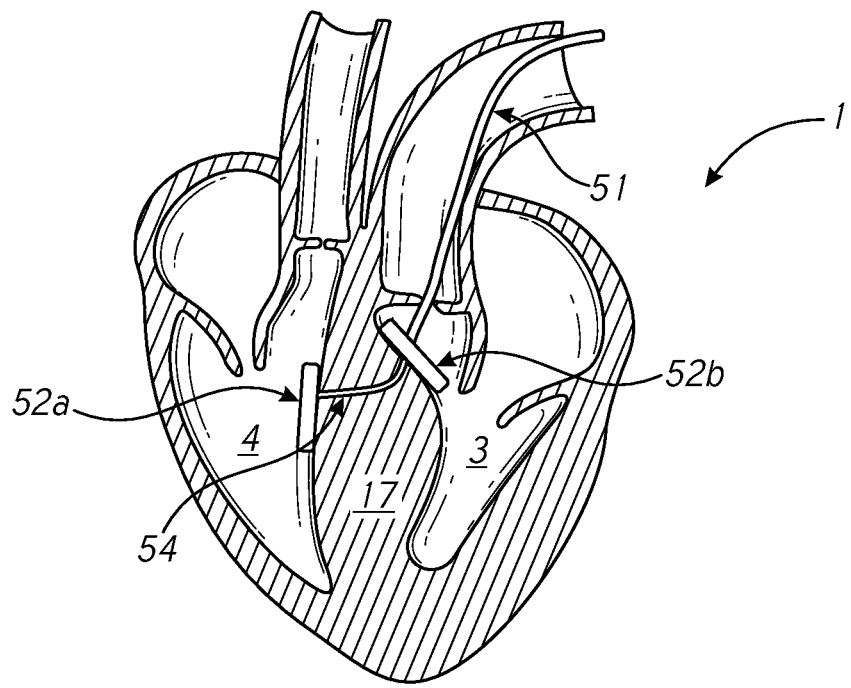

In FIG. 5D, a second anchoring element 52b may be anchored to the septum 17 wall on the left ventricle 3 side. The first anchoring element 52a and second anchoring element 52b may be connected through of a cinching device 54. In embodiments in which a guidewire is used, the cinching device 54 may be passed through and/or around the guidewire to connect to and/or pass through the first anchoring element 52a and/or second anchoring element 52b.

Figure 5E:
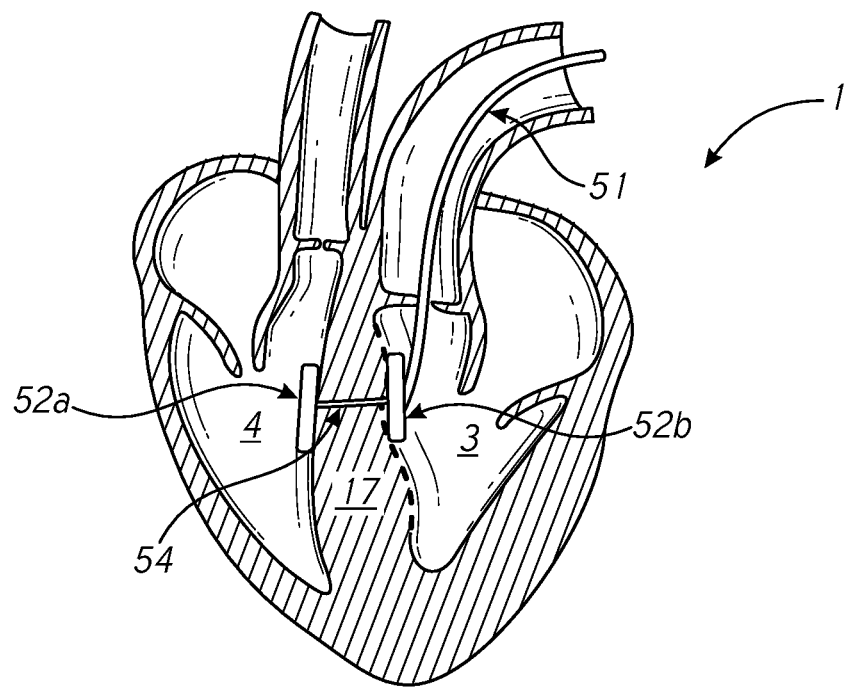

As shown in FIG. 5E, the cinching device 54 may be tightened to reduce a distance between the first anchoring element 52a and second anchoring element 52b, thereby compressing at least a portion of the thickened tissue at the septum 17. In one use case, a surgeon may pull the cinching device 54 to press the first anchoring element 52a and/or second anchoring element 52b against the septum. In another use case, the cinching device 54 may comprise a locking element that may be configured to apply pressure (e.g., via activation by a surgeon) to the first anchoring element 52a and/or second anchoring element 52b.

Figure 5F:
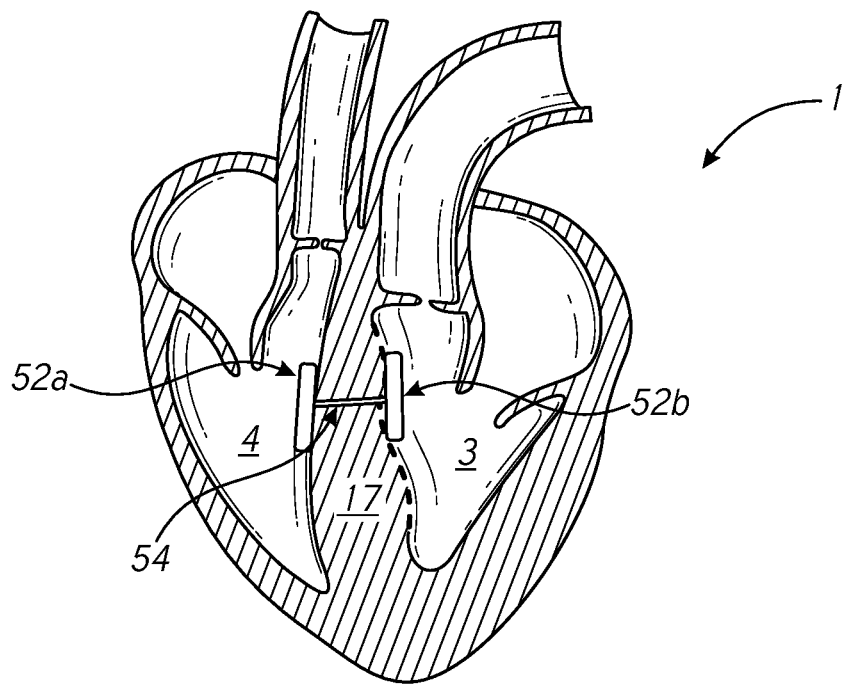

In FIG. 5F, the cinching device 54 may be locked to maintain a desired level of pressure on the septum 17. In some embodiments, the cinching device 54, first anchoring element 52a, and/or second anchoring element 52b may comprise a locking element which may be configured to lock the cinching device 54 and/or anchoring elements.

In FIG. 5G, the anchoring elements 52a and 52b and cinching device 54 may be detached from the catheter 51 (e.g., after the cinching device 54 is locked).

Figure 6:
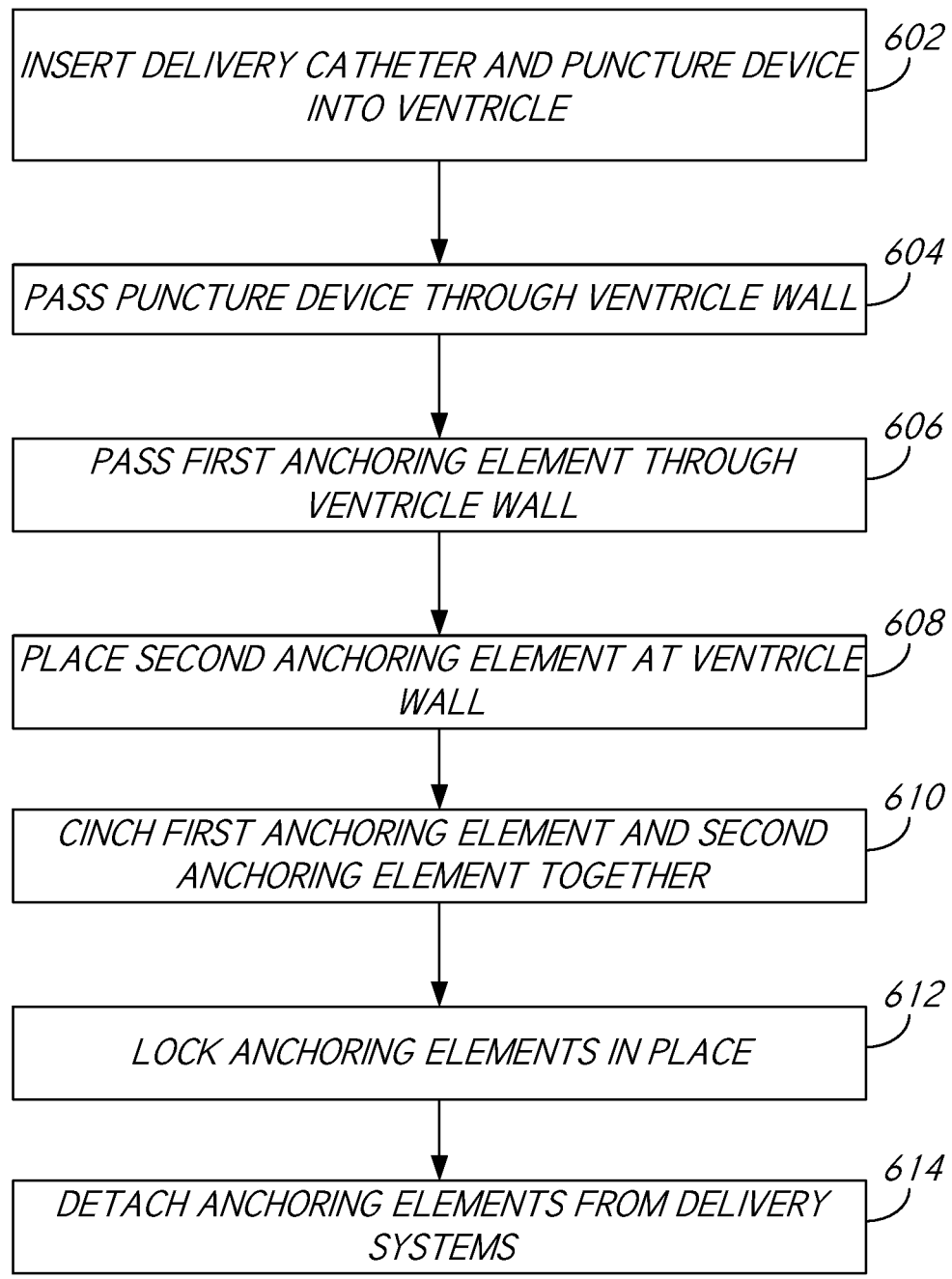
FIG. 6 provides a flowchart including various steps of another process for delivering compression devices to a heart according to one or more embodiments disclosed herein.

FIG. 6 provides a flowchart including various steps of another process 600 for delivering compression devices to a heart according to one or more embodiments disclosed herein. While some steps illustrated in FIG. 6 may be directed to delivery through the aortic valve into the left ventricle and/or through the septum into the right ventricle, such steps may also be applied to delivery into the left ventricle through the mitral valve and/or into the right ventricle through the pulmonary valve or the tricuspid valve 8 and/or through the septum into the left ventricle.

In block 602, the process 600 involves inserting a delivery catheter and/or a puncture needle or similar device into the left ventricle by way of the aortic valve, mitral valve, apex region, and/or other area of the heart. The delivery catheter may comprise any catheter, sheath, tube, and/or other device configured for delivery of various devices including needles, anchors, sutures, and/or various other devices. In some embodiments, the delivery catheter may be inserted into the heart and/or placed in close proximity to a thickened area of tissue. For example, if a septal bulge extends from the septum into the left ventricle, the delivery catheter may be delivered to the left ventricle into close proximity of the septal bulge. However, the delivery catheter may be delivered to a location that may be opposite and/or otherwise spaced apart from a thickened area of tissue. For example, if a septal bulge extends from the septum into the right ventricle, the delivery catheter may be delivered to the left ventricle side of the septum. Various needles and/or other devices passed through the catheter may be configured to penetrate tissue near the delivery catheter.

In block 604, the process 600 involves passing the puncture device (e.g., a transseptal needle) through the delivery catheter and/or through the tissue and/or a tissue wall (e.g., a ventricle wall) at or near an opening of the delivery catheter. In some embodiments, the device may be configured to penetrate the tissue at a point at or near a blood flow path. For example, the device may penetrate the tissue at a point that is within a blood flow path from the aortic valve. In other words, if a septal bulge at least partially obstructs a flow path from the aortic or other valve, the device may be configured to penetrate a point of the septal tissue that blood from the aortic or other valve flows into. The point at which the device penetrates the tissue may represent a position of a channel and/or other indentation that may be created around and/or through the thickened area of tissue.

In some embodiments, the device may have a curved form and/or may be composed of a flexible material. In some embodiments, the device may be used in connection with a dilator and/or sheath (e.g., a catheter) to deliver the device and/or penetrate the septum and/or other tissue wall. After the device punctures a surface of the tissue wall, at least a portion of the dilator and/or sheath may penetrate and/or pass at least partially through the tissue wall. The sheath may be left at least partially without the tissue wall (e.g., within the left ventricle). In some embodiments, a guidewire may be passed through the tissue wall (e.g., through a sheath) to guide one or more anchoring elements and/or lines.

In block 606, the process 600 involves passing a first anchoring element through the tissue wall (e.g., through a sheath) and/or anchoring the first anchoring element to the tissue wall. In some embodiments, the first anchoring element may be configured to be anchored to a side of the tissue wall that is opposite from a penetration point. For example, if the delivery catheter is delivered to the left ventricle, the first anchoring element may be delivered to the left ventricle and may pass through the septum to anchor to the tissue wall on the right ventricle side. In some embodiments, the first anchoring element and/or second anchoring element may be configured to be compressed (e.g., be shaped to a lower profile) during delivery in order to fit through a catheter or similar device and/or may be configured to expand after delivery. For example, the first anchoring element may be composed of Nitinol or another material with shape-memory characteristics. In some embodiments, the first anchoring element may be pre-attached to a cinching device, guidewire, and/or other device. In some embodiments, the first anchoring element may be placed and/or may be anchored to a point and/or area of the tissue wall that is at or near a blood flow path. For example, the first anchoring element may be anchored to a septal bulge and/or a portion of the septal bulge that may represent an obstruction to blood flow from the aortic valve, mitral valve, and/or other valve.

In block 608, the process 600 involves placing and/or anchoring a second anchoring element at the tissue wall. In some embodiments, the second anchoring element may be anchored at a side of the tissue wall at or near the delivery catheter. For example, if the delivery catheter is delivered to the left ventricle side of the septum, the second anchoring element may be configured to be anchored to the left ventricle side of the septum. The second anchoring element may not be configured to be passed through the tissue wall. In some embodiments, the second anchoring element may be placed and/or may be anchored to a point and/or area of the tissue wall that is at or near a blood flow path. For example, the second anchoring element may be anchored to a septal bulge and/or a portion of the septal bulge that may represent an obstruction to blood flow from the aortic valve, mitral valve, and/or other valve. The first anchoring element and second anchoring element may be configured to be connected through of a cinching device. In embodiments in which a guidewire is used, the cinching device may be passed through and/or around the guidewire to connect to and/or pass through the first anchoring element and/or second anchoring element.

In block 610, the process 600 involves tightening and/or cinching the first anchoring element and the second anchoring element together through use of a cinching device (e.g., a suture) to reduce a distance between the first anchoring element and the second anchoring element, thereby compressing at least a portion of the thickened tissue at the tissue wall. For example, tightening/cinching the cinching device may cause the first anchoring element and/or second anchoring element to press into the tissue wall and create one or more channels and/or other indentations through and/or around at least a portion of the thickened portion of the tissue wall. The channels and/or other indentations may be created at one or more portions of the tissue wall at or near a blood flow path of the heart.

In one use case, a surgeon may pull the cinching device to press the first anchoring element and/or second anchoring element against the tissue wall. In another use case, the cinching device may comprise a locking element that may be configured to apply pressure (e.g., via activation by a surgeon) to the first anchoring element and/or second anchoring element.

In block 612, the process 600 involves locking the first anchoring element, second anchoring element, and/or cinching device to maintain a desired level of pressure on the tissue wall. In some embodiments, the cinching device, first anchoring element, and/or second anchoring element may comprise a locking element which may be configured to lock the cinching device and/or anchoring elements to maintain the channel and/or other indentation through the thickened portion of the tissue wall at or near a blood flow path of the heart.

In block 614, the process 600 involves detaching the anchoring elements and/or cinching device from the catheter and/or various other delivery devices. In other words, the anchoring elements and/or cinching devices may be left in the heart as implants.

The process illustrated in FIGS. 5A-5G and 6 and/or other processes, devices, and systems disclosed herein may advantageously provide mechanisms for improving blood flow in ventricles experiencing thickened tissue walls using a fully transcatheter procedure on a beating heart. In certain embodiments, valve leaflets may not be substantially touched or damaged. Furthermore, in certain embodiments, the compression device may be designed to be retrievable.

Compression Devices

FIGS. 7A-7D illustrate example compression devices according to some embodiments. In some cases, compression devices may be configured to create greater compression on a first side of a tissue wall than on a second side of the tissue wall. For example, a thickened tissue wall may create an obstruction on only one side of the tissue wall and therefore compression may be desirable only on the side of the obstruction. Accordingly, in some embodiments compression devices may comprise multiple anchoring elements having different sizes, shapes, and/or types. As shown in FIGS. 7A-7D, a compression device may comprise a first anchoring element 72*a* and a second anchoring element. The second anchoring element 72*b* may have an elongate shape (e.g., an elongate rod) in which a length of the second anchoring element 72*b* is greater than a width of the second anchoring element. In some embodiments, the second anchoring element 72*b* may have a cylindrical shape in which a length/height of the second anchoring element 72*b* is greater than a diameter of the second anchoring element 72*b*.

The second anchoring element 72*b* may be configured for placement onto and/or near a surface of a thickened area of tissue (e.g., a septal bulge). For example, the second anchoring element 72*b* may be anchored to a side of a septum or other tissue wall that extends into a ventricle and/or other chamber. In some embodiments, the second anchoring element 72*b* may be sized and/or shaped to create a channel through a thickened area of tissue. For example, the second anchoring element 72*b* may be configured to indent only a portion of a thickened area of tissue. The portion of the thickened area of tissue may comprise less than a total surface area of the thickened area of tissue. For example, the width of the second anchoring element may be less than a width of the thickened area of tissue. Accordingly, when the second anchoring element 72*b* is placed onto the thickened area of tissue, the second anchoring element 72*b* may be configured to compress a portion of the thickened area of tissue and/or press tissue away from the portion of the thickened area of tissue that is beneath and/or around the second anchoring element 72*b*. In some use cases, the second anchoring element 72*b* may be configured for placement in the left ventricle.

In some embodiments, the second anchoring element 72*b* may be configured to be oriented in parallel with a blood flow path. For example, a length of the second anchoring element 72*b* may be configured to be approximately in-line with a valve (e.g., the aortic valve) and/or a flow path out of and/or into the valve. In this way, blood flow may be configured to pass through a channel and/or other indentation created by the second anchoring element 72*b*. In some cases, blood flow may be at least partially obstructed by a thickened area of tissue. The second anchoring element 72*b* may be configured to at least partially compress the thickened area of tissue to at least partially reduce the obstruction of the blood flow.

The first anchoring element 72a may be configured to be positioned on an opposing tissue wall with respect to the second anchoring element 72b and/or may be configured to be connected to the second anchoring element 72b through use of a cinching device 74. In some embodiments, the first anchoring element 72a may have a larger profile and/or a greater surface area than the second anchoring element 72b. For example, the first anchoring element 72a may be configured to contact a greater portion of tissue than the second anchoring element 72b. Accordingly, the first anchoring element 72a may be configured to broadly apply force to a greater surface area than the second anchoring element 72b so as to create minimal tissue disturbance at and/or around the first anchoring element 72b. The first anchoring element 72a may have any of a variety of shapes, which may include a disc (e.g., as illustrated in FIG. 7A), two intersecting rods (e.g., in an "X" shape, as shown in FIG. 7B), more than two intersecting rods (e.g., as shown in FIG. 7C), and a spiral wire form (e.g., as shown in FIG. 7D).

Figure 7A:
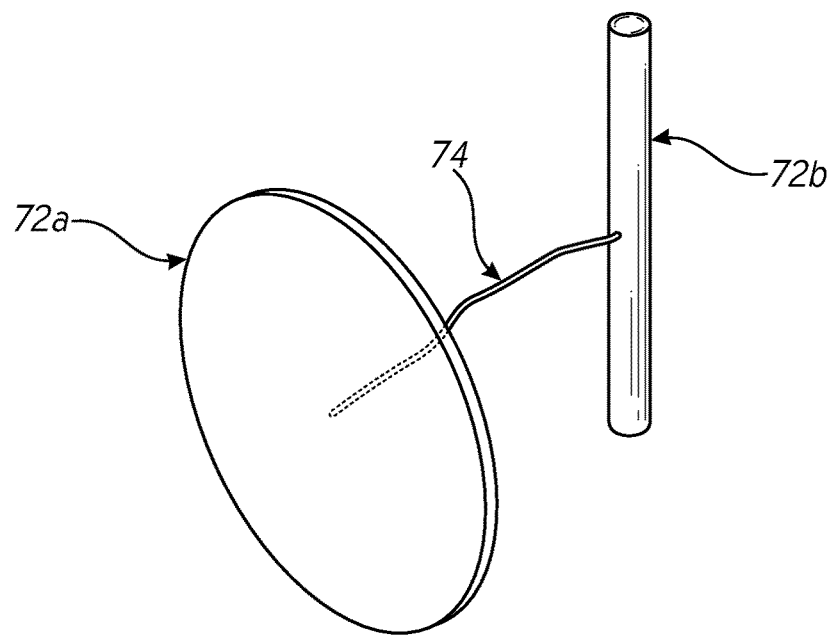
FIGS. 7A-7D illustrate example anchoring elements according to some embodiments.
Figure 7B:
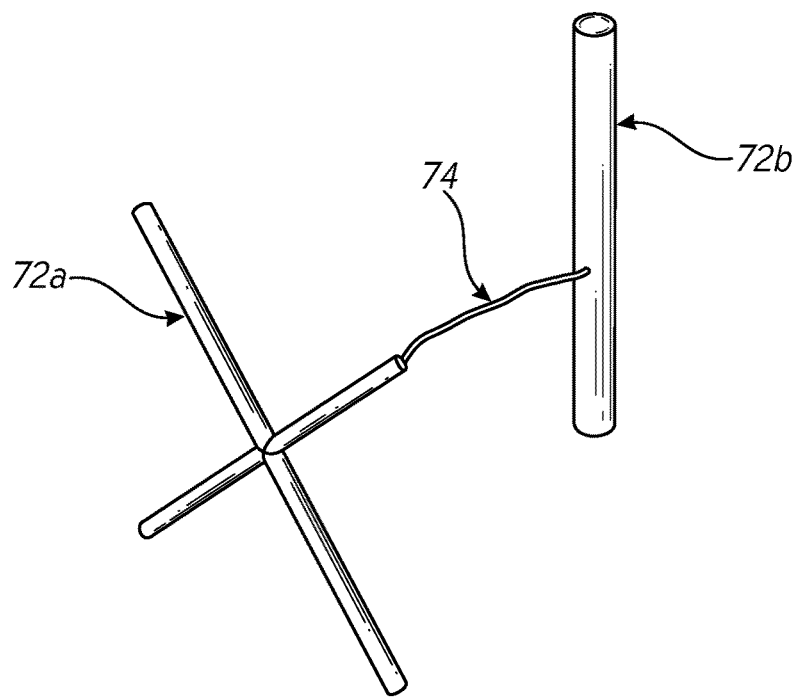
Figure 7C:
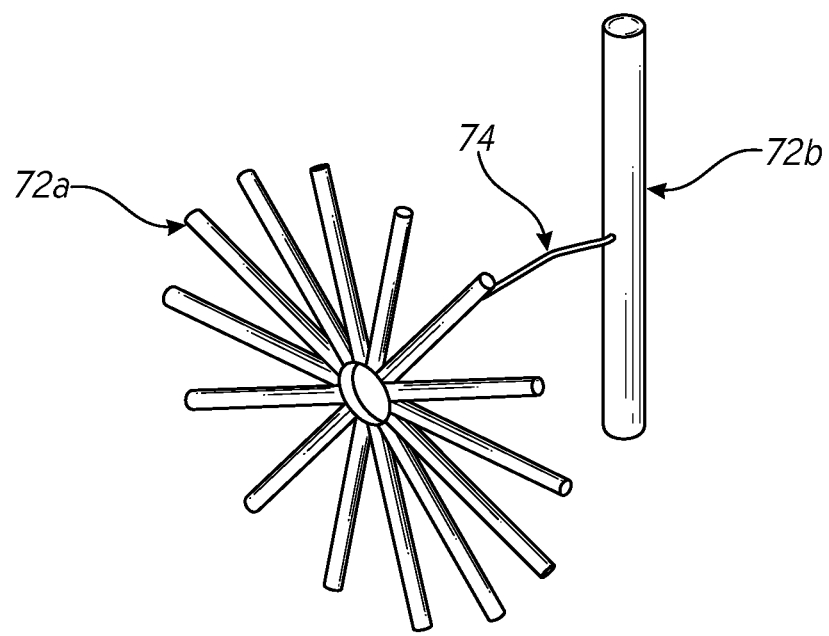
Figure 7D:
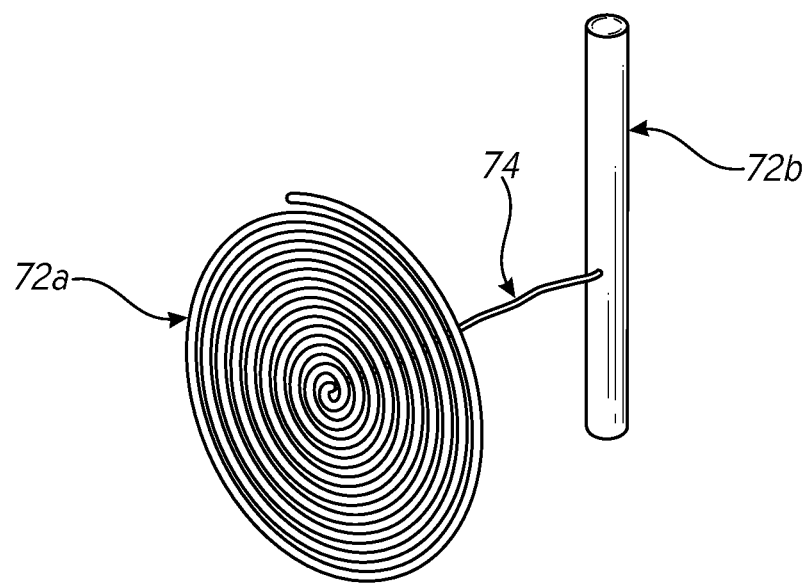

As shown in FIG. 7A, the first anchoring element 72a may have the shape of a disc and/or may have circular and/or elliptical shape. In some embodiments, the first anchoring element 72a may have a diameter and/or width that is approximately equal to a length of the second anchoring element 72b. The width of the second anchoring element 72b may be smaller (e.g., 5× smaller) than the diameter and/or width of the first anchoring element 72a. The first anchoring element 72a may be configured to cover a larger surface area than the second anchoring element 72b such that the first anchoring element 72a may cause a smaller degree of indentation of the tissue at and/or around the first anchoring element 72a than the second anchoring element 72b may cause at and/or around the second anchoring element 72b.

In cases in which the first anchoring element 72a comprises multiple intersecting rods (see, e.g., FIGS. 7B and 7C), each of the rods may have a length that is approximately equal to a length of the second anchoring element 72b. Similarly, a width of a rod of the first anchoring element 72a may be approximately equal to or smaller than a width of the second anchoring element 72b. The multiple intersecting rods may form "spokes" of an elliptical and/or circular area about the first anchoring element 72a. Similarly, a first anchoring element 72a forming a spiral wire form (see FIG. 7D) may form an elliptical and/or circular area having a diameter approximately equal to a length of the second anchoring element 72b.

In some embodiments, the first anchoring element 72a and/or second anchoring element 72b may be composed of a shape memory material (e.g., Nitinol). In this way, an anchoring element may maintain a lower profile during insertion through a catheter and/or sheath and may expand to a larger form after exiting the catheter and/or sheath. In some embodiments, components of an anchoring element may be separate during delivery and may be joined after delivery. For example, the intersecting rods shown in FIG. 7B may be delivered separately and may join together after passing through the septum 17. One or both of the rods may have a notch or similar mechanism to guide the rods to joining in a desired manner. In some embodiments, the spiral wire form shown in FIG. 7D may be delivered as a flexible wire that forms a spiral form after exiting a catheter and/or sheath.

Cinching Devices

FIGS. 8A-8F illustrate example cinching devices according to some embodiments. In some embodiments, a cinching device 80 may be configured to connect to and/or pass through two or more anchoring elements 82a, 82b.

Figure 8A:
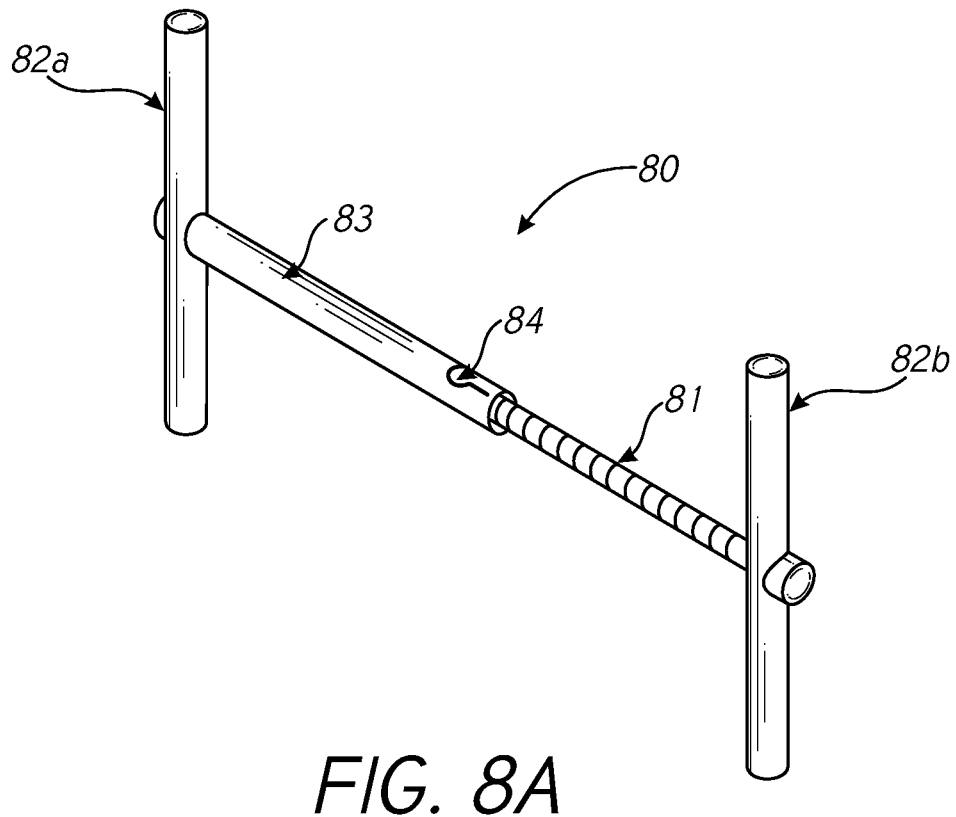
FIGS. 8A-8F illustrate example cinching devices according to some embodiments.

As shown in FIG. 8A, the cinching device 80 may comprise a slotted rod 81 (e.g. connected to a second anchoring element 82b) and/or a locking tube 83 (e.g., connected to a first anchoring element 82a). In some embodiments, the slotted rod 81 may be configured to fit at least partially into the locking tube 83. The slotted rod 81 may have an engagement mechanism (e.g., one or more grooves and/or a continuous helical groove or thread along the slotted rod 81) that may be configured to engage with an engagement mechanism on the locking tube 83 (e.g., a locking prong 84 or a helical groove or thread along the inside of the locking tube 83). For example, the locking prong 84 may comprise a peg or other protruding device that is configured to fit into a groove of the slotted rod 81. In some embodiments, the locking prong 84 may be shaped or otherwise configured to allow movement of the slotted rod 81 into the locking tube 83 but may prevent movement of the slotted rod 81 out of the locking tube 83. The locking prong 84 may be pressed or otherwise activated to release the slotted rod 81. For example, locking prongs 84 may be engaged by an internal tube that may allow free movement of the slotted rod 81.

In one use case, the slotted rod 81 may comprise a helical groove that is configured to receive a helical thread of the tube 83 such that the slotted rod 81 and/or tube 83 may be twisted to move the slotted rod 81 into the tube 83. The engagement mechanisms of the slotted rod 81 and/or tube 83 may be configured such that when the slotted rod 81 is inserted into the tube, the slotted rod 81 may be held in place and/or may be removed by a certain action (e.g., twisting the slotted rod 81 and/or tube 83 in a particular direction).

The cinching device 80 may be configured to apply force to the anchoring element 82a, 82b to move the anchoring elements 82a, 82b closer together. For example, by inserting the slotted rod 81 further into the tube 83, a distance between a first anchoring element 82a and a second anchoring element 82b may be reduced. In this way, one or more of the anchoring elements 82a, 82b may apply increased pressure to a tissue wall to create a channel in the tissue wall.

In some embodiments, the first anchoring element 82a and/or second anchoring element 82b may be configured to rotate around the cinching device 80. In this way, the first anchoring element 82a and/or second anchoring element 82b may be oriented in a desired direction. For example, the second anchoring element 82b may have a rod-like shape and may be configured to create a channel in a thickened area of tissue. The second anchoring element 82b may be rotated to create a channel having a desired orientation/direction in the area of tissue to improve blood flow. In some embodiments, the slotted rod 81 and/or tube 83 may be configured to be embedded in the septum 18 or other tissue wall.

Figure 8B:
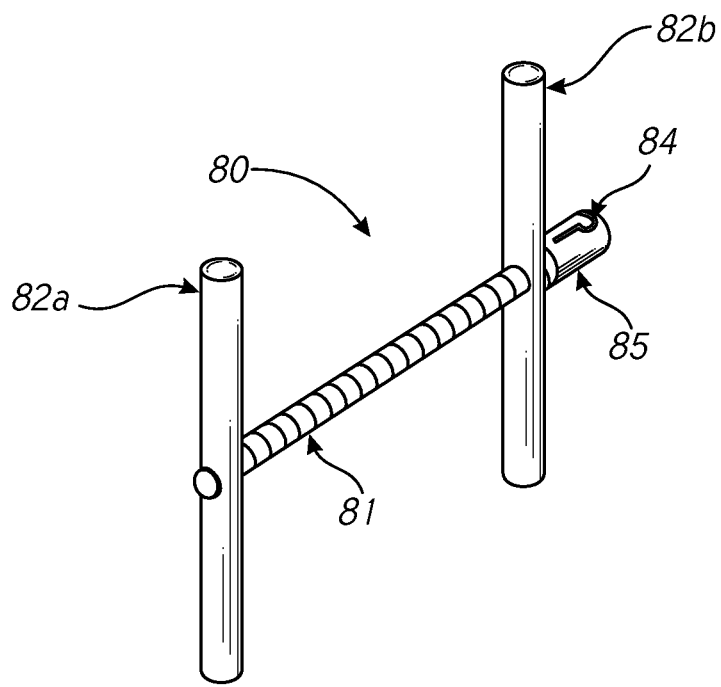

As shown, for example, in FIG. 8B, the cinching element 80 may comprise a slotted rod 81 (e.g., connected to the first anchoring element 82a and second anchoring element 82b) and/or a locking element 85 (connected to an end of the slotted rod 81). In some embodiments, the slotted rod 81 may have an engagement mechanism (e.g., a continuous helical groove or thread along the slotted rod 81) that may be configured to engage with an engagement mechanism in the locking element 85 (e.g., a locking prong 84 or a helical groove or thread along the inside of the locking element 85). In one use case, the locking prong 84 may comprise a peg or other protruding device that is configured to fit into a groove of the slotted rod 81. In some embodiments, the locking prong 84 may be shaped or otherwise configured to allow movement of the slotted rod 81 into the locking element 85 but may prevent movement of the slotted rod 81 out of the locking element 85. The locking prong 84 may be pressed or otherwise activated to release the slotted rod 81. For example, locking prongs 84 may be engaged by an internal tube that may allow free movement of the slotted rod 81.

In another use case, the slotted rod 81 may comprise a helical groove that is configured to receive a helical thread of the locking element 85 such that the slotted rod 81 and/or locking element 85 may be twisted to move the slotted rod 81 into the locking element 85.

The locking element 85 may be configured to apply force to the first anchoring element 82*a* and/or second anchoring element 82*b* to move the anchoring elements 82*a*, 82*b* closer together. For example, by inserting the slotted rod 81 further into the locking element 85, a total length of the cinching device 80 may be reduced and the locking element 85 may push the second anchoring element 82*b* towards the first anchoring element 82*a* such that a distance between the first anchoring element 82*a* and the second anchoring element 82*b* may be reduced. In this way, one or more of the anchoring elements 82*a*, 82*b* may apply increased pressure to a tissue wall to create a channel in the tissue wall.

In some embodiments, the slotted rod 81 may be configured to be embedded in the septum 18 or other tissue wall. The locking element 85 may be configured to be situated in a ventricle or other chamber (e.g., outside of the tissue wall).

Figure 8C:
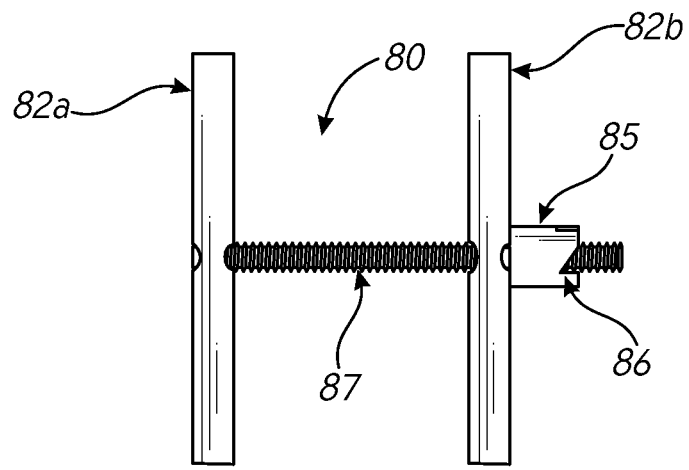

As shown in FIG. 8C, for example, the cinching element 80 may comprise a threaded rod 87 (e.g., connected to the first anchoring element 82*a* and second anchoring element 82*b*) and/or a locking element 85 (e.g., connected to an end of the threaded rod 87). In some embodiments, the threaded rod 87 may have an engagement mechanism (e.g., a continuous helical thread along the threaded rod 87) that may be configured to engage with an engagement mechanism in the locking element 85 (e.g., a helical groove along the inside of the locking element 85). For example, the threaded rod 87 may comprise a helical thread that is configured to fit into a helical groove of the locking element 85 such that the threaded rod 87 and/or locking element 85 may be twisted to move the threaded rod 87 into the locking element 85. The locking element 85 may be configured to apply force to the first anchoring element 82*a* and/or second anchoring element 82*b* to move the anchoring elements 82*a*, 82*b* closer together. For example, by inserting the threaded rod 87 further into the locking element 85, the locking element 85 may push the second anchoring element 82*b* towards the first anchoring element 82*a* such that a distance between a first anchoring element 82*a* and a second anchoring element 82*b* may be reduced. In this way, one or more of the anchoring elements 82*a*, 82*b* may apply increased pressure to a tissue wall to create a channel in the tissue wall.

The threaded rod 87 may be configured to be embedded in the septum 18 or other tissue wall. The locking element 85 may be configured to be situated in a ventricle or other chamber (e.g., outside of the tissue wall).

In some embodiments, the first anchoring element 82*a* and/or second anchoring element 82*b* may comprise engagement mechanisms for engaging with the cinching device 80. For example, the first anchoring element 82*a* and/or second anchoring element 82*b* may comprise one or more cavities for receiving the cinching device 80. The one or more cavities may have helical threads and/or grooves for engaging corresponding mechanisms of the cinching device 80. For example, by twisting the second anchoring element 82*b* and/or cinching device 80, the second anchoring element 82*b* may move along the length of the cinching device 80 due to helical engagement mechanisms of the second anchoring element 82*b* and/or cinching device 80.

In some embodiments, the locking element 85 may have one or more notches 86 to interface with a catheter or other delivery device. For example, an end of a catheter may be configured to fit into the notches 86 to allow a surgeon to twist the locking element.

Figure 8D:
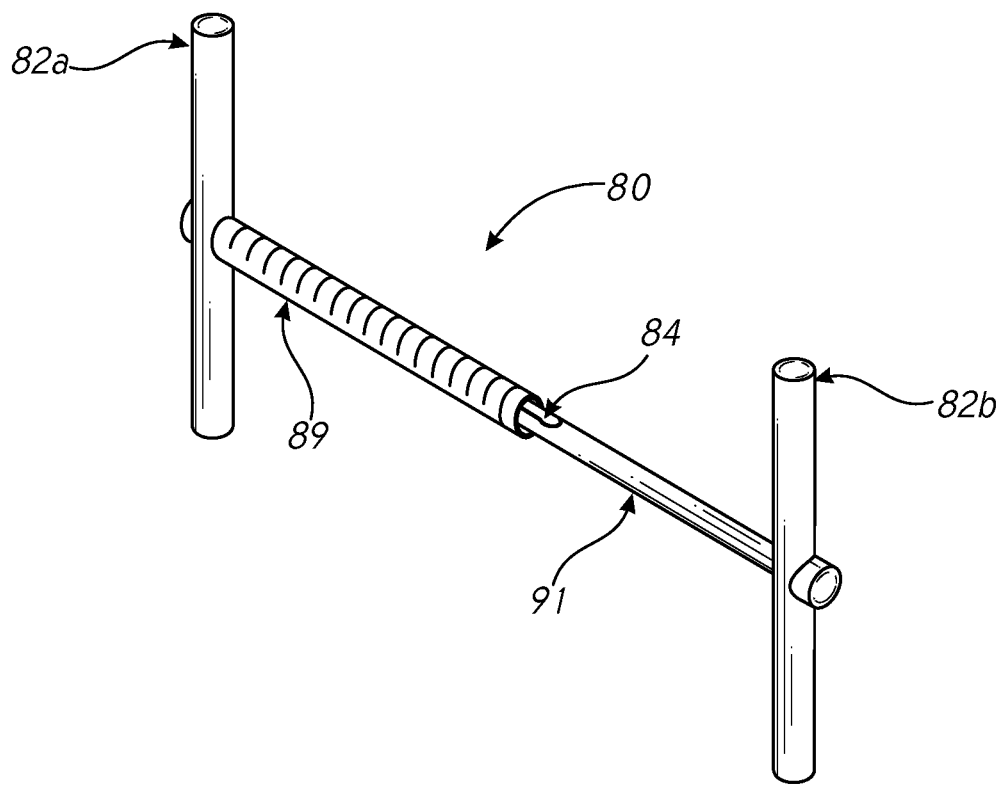

As shown in FIG. 8D, the cinching device 80 may comprise a slotted tube 89 (e.g. connected to a first anchoring element 82*b*) and/or a locking rod 91 (e.g., connected to a second anchoring element 82*b*). In some embodiments, the locking rod 91 may be configured to fit at least partially into the slotted tube 89. The locking rod 91 may have an engagement mechanism (e.g., a locking prong 84) that may be configured to engage with an engagement mechanism on the slotted tube 89 (e.g., a helical groove or thread along the inside and/or outside of the locking tube 89). For example, the slotted tube 89 may comprise a helical groove that is configured to receive at least a portion of the locking prong 84 (e.g., a protruding peg) when the locking rod 91 is pushed into the slotted tube 89. The engagement mechanisms of the slotted tube 89 and/or locking rod 91 may be configured such that when the locking rod 91 is inserted into the slotted tube 89, the locking rod 91 may be held in place and/or may be removed by a certain action (e.g., engaging/pressing the locking prong 84). In some embodiments, the slotted tube 89 and/or locking rod 91 may be configured to be embedded in the septum 18 or other tissue wall.

Each of the slotted rod 81, locking tube 83, threaded rod 87, slotted tube 89, and locking rod 91 may be composed of Nitinol, Teflon, metal, plastic, polymer or other material and may have a rigid or flexible form. For example, the threaded rod 87 may be composed of a flexible Nitinol cord comprising threads. In some embodiments, the rods/tubes may be composed of multiple components, for example several elements along a flexible wire (similar to a beaded necklace).

Figure 8E:
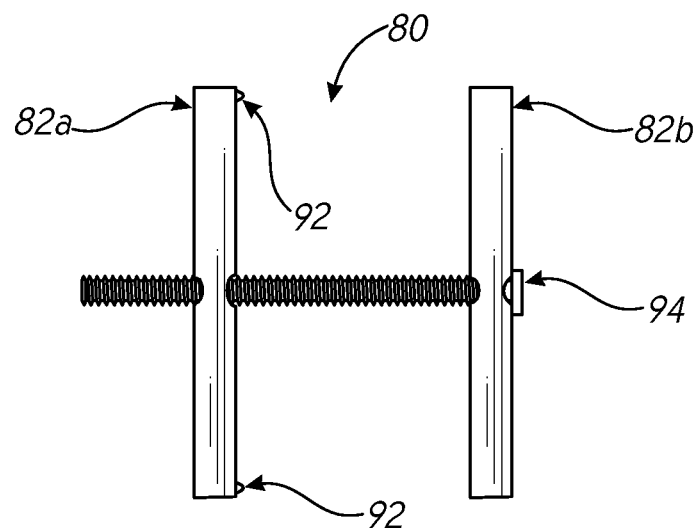

As shown in FIG. 8E, the first anchoring element 82*a* and/or second anchoring element 82*b* may comprise one or more mini anchors 92. While only the first anchoring element 82*a* is shown comprising mini anchors 92 in FIG. 8E, the second anchoring element 82*b* may also or alternatively comprise one or more mini anchors 92. Moreover, while the first anchoring element 82*a* comprises two mini anchors 92 in the example shown in FIG. 8E, an anchoring element 82*a*, 82*b* may comprise a single mini anchor 92 or more than two mini anchors 82*b*.

The mini anchor(s) 92 may be configured to pierce or otherwise engage the septum or other tissue wall to prevent the first anchoring element 82*a* and/or second anchoring element 82*a* from moving (e.g., rotating) after delivery. In some embodiments, the mini anchor(s) 92 may be configured to be fixed into trabeculae of a ventricle of a heart. For example, the trabeculae may generally have cobweb-like tissue features, wherein the mini anchor(s) 92 can pierce and/or become intentionally entangled behind or within such tissue features. The tissue features of the trabeculae may present gaps between ridges or other features, wherein the mini anchor(s) can be navigated into such gaps and/or behind ridges in the trabeculae tissue. Although engaging with trabeculae is described herein, it should be understood that the mini anchor(s) 92 may leverage any structural element inside the ventricle of the heart.

One or both of the first anchoring element 82*a* and second anchoring element 82*b* may rotate to increase and/or decrease a distance between the anchoring elements. For example, the first anchoring element 82a may be rotated around the cinching device 80 to reduce a distance of the first anchoring element 82a from the second anchoring element 82b and increase applied pressure to a tissue wall between the anchoring elements. When a desired distance between the anchoring elements is reached, the mini anchor(s) 92 may prevent further rotation of the first anchoring element 82a. In some embodiments, the cinching device 80 may comprise a head element 94 at one or both ends of the cinching device 80 to prevent movement of the second anchoring element 82b and/or first anchoring element 82a.

Figure 8F:
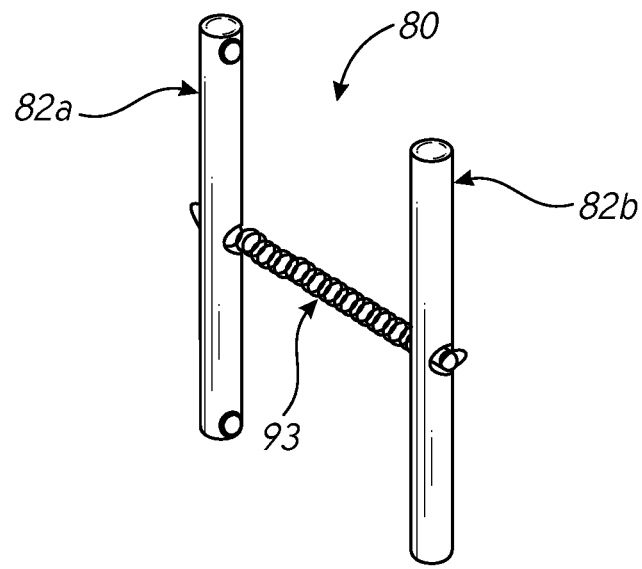

As shown in FIG. 8F, the cinching device 80 may comprise a twisted rod 93 comprising one or more twisted cords, bands, sutures, wires, or other devices. For example, the twisted rod 93 may comprise two sutures twisted together. By twisting the sutures, the cinching device 80 may be tightened (e.g., a distance between the first anchoring element 82a and second anchoring element 82b may be reduced).

In some embodiments, one or both ends of the twisted rod 93 may comprise a locking element for preventing the first anchoring element 82a and/or second anchoring element 82b from becoming disconnected from the twisted rod 93. Moreover, the twisted rod 93, first anchoring element 82a, and/or second anchoring element 82b may comprise a notch or similar device to allow the twisted rod 93 to be twisted in only one direction.

In some embodiments, the first anchoring element 82 and/or second anchoring element 82b may be connected to the cinching device 80 via one or more hinges or similar devices to allow rotation of the anchoring elements at any angle to allow the anchoring elements to conform to any size/shape of tissue wall.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

What is claimed is:

1. A cardiac device comprising:
    a first anchoring element configured to be anchored to a first side of a tissue wall, the first anchoring element having a cylindrical shape, wherein a diameter of the first anchoring element is less than a length of the first anchoring element;
    a second anchoring element configured to be anchored to a second side of the tissue wall; and
    a cinching device comprising a tube attached to and extending between the first anchoring element and the second anchoring element, the tube configured to:
        extend through the tissue wall; and
        apply force to the first anchoring element to move the first anchoring element towards the second anchoring element and at least partially compress the first side of the tissue wall.

2. The cardiac device of claim 1, wherein the first anchoring element is configured to form an indentation at the first side of the tissue wall.

3. The cardiac device of claim 1, wherein the first anchoring element is configured to form a flow channel at the first side of the tissue wall.

4. The cardiac device of claim 3, wherein the flow channel is situated below an aortic valve to facilitate blood flow into the aortic valve.

5. The cardiac device of claim 4, wherein the first anchoring element is configured to anchor to the first side of the tissue wall with the length of the first anchoring element extending in line with an aorta.

6. A cardiac device comprising:
    a first anchoring element configured to be anchored to a first side of a tissue wall and configured to form a flow channel at the first side of the tissue wall;
    a second anchoring element configured to be anchored to a second side of the tissue wall; and
    a cinching device comprising a tube attached to and extending between the first anchoring element and the second anchoring element, the tube configured to:
        extend through the tissue wall; and
        apply force to the first anchoring element to move the first anchoring element towards the second anchoring element and at least partially compress the first side of the tissue wall.

7. The cardiac device of claim 1, wherein the cinching device is rigid.

8. The cardiac device of claim 1, wherein the cinching device is flexible.

9. The cardiac device of claim 1, wherein the cinching device comprises one or more rigid mechanisms.

10. The cardiac device of claim 9, wherein the tube comprises one or more rigid mechanisms.

11. The cardiac device of claim 1, wherein the tube comprises one or more mechanisms configured to move the first anchoring element towards the second anchoring element and at least partially compress the first side of the tissue wall.

12. The cardiac device of claim 11, wherein the one or more mechanisms comprise a notch.

13. The cardiac device of claim 1, wherein the cinching device comprises multiple tubes.

14. The cardiac device of claim 6, wherein the tube comprises one or more rigid mechanisms.

15. The cardiac device of claim 6, wherein the tube comprises one or more mechanisms configured to move the first anchoring element towards the second anchoring element and at least partially compress the first side of the tissue wall.

16. The cardiac device of claim 15, wherein the one or more mechanisms comprise a notch.

17. The cardiac device of claim 6, wherein the cinching device comprises multiple tubes.

18. A method comprising:
    anchoring a first anchoring element to a first side of a tissue wall, the first anchoring element having a cylindrical shape, wherein a diameter of the first anchoring element is less than a length of the first anchoring element;
    anchoring a second anchoring element to a second side of the tissue wall;
    attaching a cinching device comprising a tube to the first anchoring element and the second anchoring element;
    extending the cinching device and tube through the tissue wall; and
    applying force, via the tube, to the first anchoring element to move the first anchoring element towards the second anchoring element and at least partially compress the first side of the tissue wall.

19. The method of claim 18, further comprising tightening the tube to apply force to the first anchoring element to move the first anchoring element towards the second anchoring element and at least partially compress the first side of the tissue wall.

20. The method of claim 18, wherein the cinching device comprises multiple tubes.

* * * * *